United States Patent [19]
Griffith et al.

[11] Patent Number: 5,115,814
[45] Date of Patent: May 26, 1992

[54] INTRAVASCULAR ULTRASONIC IMAGING PROBE AND METHODS OF USING SAME

[75] Inventors: James M. Griffith, Newport Beach; Paul J. Zalesky, Huntington Beach; James M. Gessert, Newport Beach; Viet P. Dinh; James D. Passafaro, both of Santa Ana, all of Calif.

[73] Assignee: InterTherapy, Inc., Costa Mesa, Calif.

[21] Appl. No.: 395,839

[22] Filed: Aug. 18, 1989

[51] Int. Cl.⁵ .............................................. A61B 8/12
[52] U.S. Cl. ........................... 128/662.06; 128/660.03
[58] Field of Search ............... 128/660.03, 662.06; 606/46

[56] References Cited

U.S. PATENT DOCUMENTS

| | | | |
|---|---|---|---|
| 3,817,089 | 6/1974 | Eggleton et al. | 128/662.06 |
| 3,938,502 | 2/1976 | Bom. | |
| 3,942,530 | 3/1976 | Northeved | 606/46 |
| 4,319,580 | 3/1982 | Colley et al. | 128/662.06 |
| 4,354,501 | 10/1982 | Colley et al. | 128/662.06 |
| 4,374,525 | 2/1983 | Baba | 128/660 |
| 4,391,282 | 7/1983 | Ando et al. | 128/662.06 |
| 4,408,612 | 10/1983 | Utsugi | 128/662.06 |
| 4,442,842 | 4/1984 | Baba | 128/662.06 |
| 4,466,443 | 8/1984 | Utsugi | 128/662.06 |
| 4,466,444 | 8/1984 | Baba | 128/662.06 |
| 4,489,727 | 12/1984 | Matsuo et al. | 128/660 |
| 4,489,728 | 12/1984 | Matsuo et al. | 128/660 |
| 4,494,549 | 1/1985 | Namba et al. | 128/662.06 |
| 4,546,771 | 10/1985 | Eggleton et al. | 128/660 |
| 4,572,201 | 2/1986 | Kondo et al. | 128/662.06 |
| 4,582,067 | 4/1986 | Silverstein et al. | 128/662.06 |
| 4,641,657 | 2/1987 | Ellis | 128/662.03 X |
| 4,732,156 | 3/1988 | Nakamura | 128/660 |
| 4,794,931 | 1/1989 | Yock | 128/660 |
| 4,841,977 | 6/1989 | Griffith et al. | 128/662.06 |
| 4,887,605 | 12/1989 | Angelsen et al. | 128/303.1 |
| 4,899,757 | 2/1990 | Pope, Jr. et al. | 128/662.06 |
| 4,917,097 | 4/1990 | Proudian et al. | 128/660 |
| 4,917,104 | 4/1990 | Rebell | 128/772 |
| 4,920,967 | 5/1990 | Cottonaro et al. | 128/662.06 |
| 4,928,699 | 5/1990 | Sasai | 128/662.06 |
| 4,951,677 | 8/1990 | Crowley et al. | 128/662.06 |
| 4,991,588 | 2/1991 | Pfleuger et al. | 128/772 X |
| 4,998,916 | 3/1991 | Hammerslag et al. | 128/772 X |
| 5,007,434 | 4/1991 | Doyle et al. | 128/772 |
| 5,049,130 | 9/1991 | Powell | 604/96 |

FOREIGN PATENT DOCUMENTS 2305501 8/1974 Fed. Rep. of Germany.
2424733 11/1979 France.

OTHER PUBLICATIONS

Wild et al., "Ultrasonic Ranging" Electronics 174-180 (Mar. 1955).
Ebina et al., "The Diagnostic Application of Ultrasound to the Disease in Mediastinal Organs", Sci. Rep. Res. Inst. Tohoku U. 12:199-212.
Wells, P. N. T., "Developments in Medical Ultrasonics", European Symposium on Medical Electronics, pp. 272-276 (Oct. 1975).
Kossoff, G., "Diagnostic Applications of Ultrasound in Cardiology", Australas Radiol., X:101-6 (1966).

(List continued on next page.)

*Primary Examiner*—Francis Jaworski
*Attorney, Agent, or Firm*—Nixon & Vanderhye

[57] ABSTRACT

An intravascular ultrasonic imaging probe includes a transducer subassembly adapted to being rotated within a guide catheter via a drive cable. The guide catheter establishes a bearing surface for supporting the transducer subassembly during rotation while also mechanically isolating the rotating transducer subassembly from surrounding tissue (thereby protecting the tissue from inadvertent and/or undesired tissue abrasion by the subassembly during rotation). The catheter is positioned within a vessel to be imaged by telescopically advancing the same over a previously positioned guide wire, the guide wire being withdrawn after the guide catheter is positioned. Thereafter, the imaging probe is inserted into the guide catheter and operated so as to obtain ultrasonic images of the vessel under investigation.

52 Claims, 8 Drawing Sheets

OTHER PUBLICATIONS

Omoto, R., "Ultrasonic Tomography of the Heart: an Intracardiac Scan Method" Ultrasonics, pp. 80-83, (Apr. 1967).

Omoto, R., "Intracardiac Scanning of the Heart with the Aid of Ultrasonic Intravenous Probe", Jap. Heart J. 8:569-581 (1967).

Eggleton et al., "Computerized Ultrasonic Visualization of Dynamic Ventricular Configurations", 8th ICMBE, Chicago, Ill. (Jul. 1969).

Hartley et al., "A Single-Crystal Ultrasonic Catheter-Tip Velocity Probe" Medical Instrumentation 8:241-243.

Hisanaga et al., "A New Real-Time Sector Scanning System of Ultra-Wide Angle . . . ", Proc. of the 22nd Annual Mtg of the AIUM, (1978).

Gichard et al., "Development of a Mechanically Scanned Doppler Blood Flow Catheter", Ultrasonics Symposium Proc. 75, CHO-994-4SU, pp. 18-21 (1975).

Wells et al., "Untitled" Conference: Advances in Bioengineering, San. Fran., Calif. (Dec. 1978).

Bertini et al., "Rotating Probe for Trans-Esophageal Cross-Sectional Echocardiography", J. Nucl. Med. Allied. Sci. 28(2):115-121.

Fukuda, M., "Endoscopic Ultrasonography", In: Gill, R. W., Dadd, M. J., eds., WFUMB '85, 13-16 (1985).

Bom et al., "Ein Weg sur intraluminaren Echoarteriographie" Untraschall 8 pp. 233-236, (Oct. 1987) (translation attached).

Isner, et al., "Percutaneous Intravascular US as Adjunct to Catheter-based Interventions: . . . Radiology"; 1990; 175(1):61-70.

Crowley, et al., "Optimized Ultrasound Imaging Catheters for use in the Vascular System", Int. J. Card. Imag. 1989; 4:145-151.

Bom et al., "Early and Recent Intraluminal Ultrasound Devices", International Journal of Cardiac Imaging, 4: 79-88 (1989).

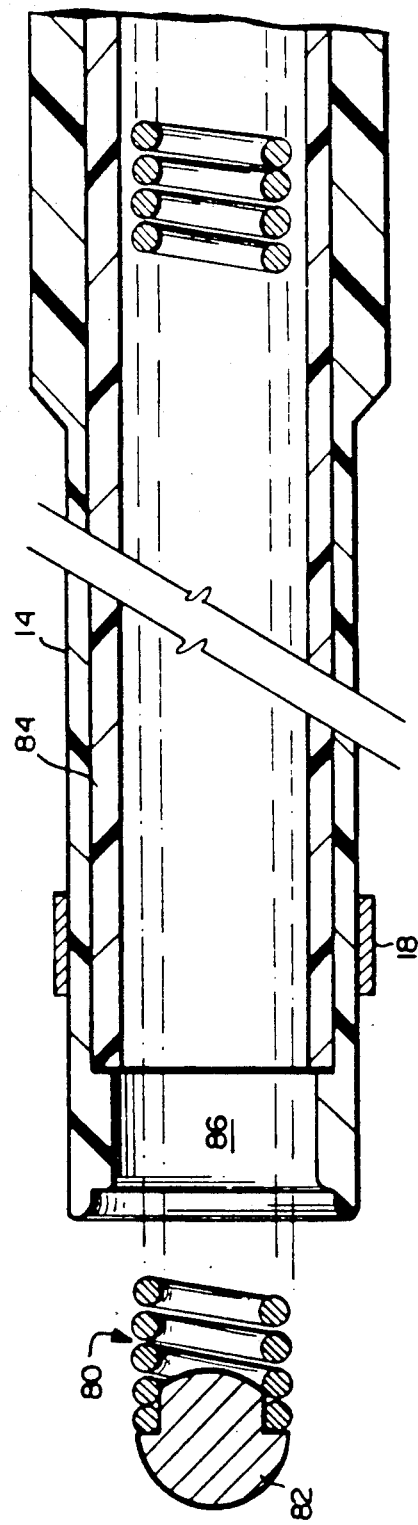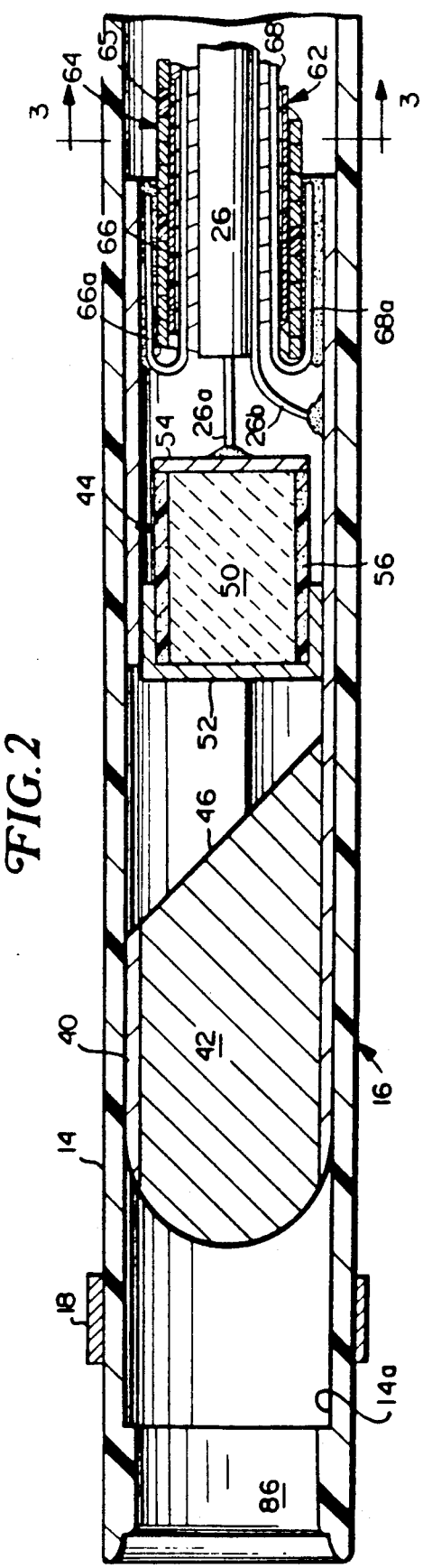

FIG. 10a
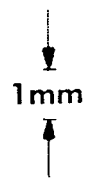
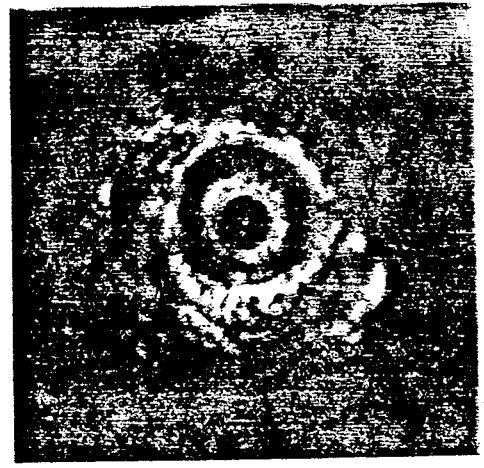
RATE = 3mm, DIAMETER = 8mm
FIG. 10b
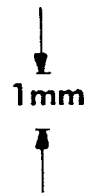
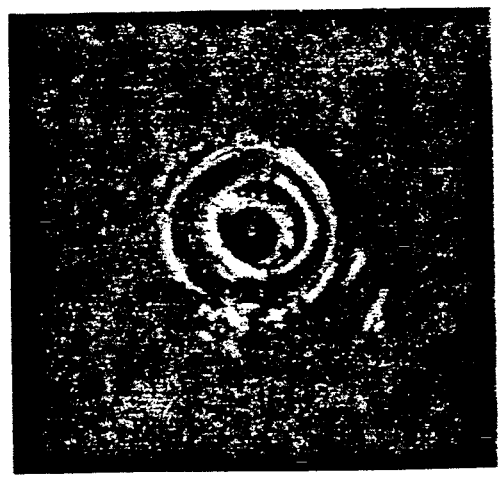
RATE = 3mm, DIAMETER = 8mm

FIG. 11a
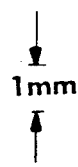
RATE = 3mm, DIAMETER = 8mm
FIG. 11b
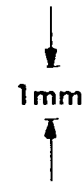
RATE = 3mm, DIAMETER = 8mm

INTRAVASCULAR ULTRASONIC IMAGING PROBE AND METHODS OF USING SAME

RELATED PATENTS AND APPLICATIONS

This application is related to commonly owned U.S. Pat. No. 4,841,977 issued on Jun. 27, 1989, and to commonly owned, copending U.S. Pat. application Ser. No. 07/158,761, filed on Feb. 22, 1988, the entire content of each being expressly incorporated hereinto by reference.

FIELD OF INVENTION

The present invention relates to the field of intravascular ultrasonic imaging devices and methods —that is, devices and methods which utilize acoustic transducers operating at ultrasonic frequencies to image intravascular geometry and/or associated tissue characteristics. In preferred forms, the invention is embodied in an elongate probe guide assembly which is operable within a guide catheter having a distal portion relatively transparent to ultrasonic energy. The probe includes an ultrasonic imaging subassembly which radially redirects ultrasonic imaging waves and returning "echo" waves relative to the probe's elongate axis. This subassembly is rotated using the interior of the guide catheter as a rotation bearing so that 360° intravascular imaging is effected.

BACKGROUND AND SUMMARY OF THE INVENTION

Intravascular probes which include ultrasound imaging crystals are well known. For example, it has previously been proposed to mount a piezoelectric crystal element (conventionally termed a "transducer") on or within a catheter of the type which can be inserted into a blood vessel. Once the probe has been inserted into a blood vessel, the transducer is electro-mechanically excited (as by the application of an electrical signal) to cause emission of ultrasonic energy into the surrounding tissue. While much of the emitted energy is absorbed by the surrounding tissue, a sufficient amount of energy is reflected back toward the transducer to permit imaging (with reflection occurring principally at the interfaces between different types of biological material, e.g., the interface between blood and the vascular wall, the interface between blood and lesions adhered to the vascular wall etcetera).

The transducer, in turn, produces weak electrical signals in response to electro-mechanical excitation by the returning reflected ("echo") ultrasonic energy. These weak electrical signals can be used to determine the geometry and/or other characteristics of the blood vessel, for example, to determine whether or not the blood vessel contains lesions or other abnormalities. These determinations are usually termed "imaging" since suitable video and/or other signal monitoring equipment are employed to convert the weak electrical signals produced by the transducer into human-readable form. Information gained from such imaging thus may assist the physician in a vascular treatment in real time or in diagnosing a patient's particular ailment or disease so that suitable therapy can be prescribed.

Intravascular imaging through 360° has also been proposed. For example, in the above-referenced U.S. Pat. No. 4,841,977, novel intravascular ultrasonic imaging probes are disclosed having transducer arrays which include radially spaced-apart transducers. These radially spaced apart transducers thereby image corresponding radial segments of the vessel interior under examination (with conventional algorithms being utilized when necessary to "fill in" missing image segments through interpolation and/or partial images to provide sufficient information to a viewer).

It has also recently been proposed in U.S. Pat. No. 4,794,931 to Yock to provide intravascular imaging probes with a stationary transducer and an ultrasonic wave reflector which is rotatable and longitudinally movable relative to the transducer. (See, FIGS. 10 and 11 of Yock '931, and the corresponding description thereof). Moreover, it will be observed that the imaging devices disclosed in Yock '931 are each provided with a forwardly extending guide wire which serves to guide or steer the housing (which includes the transducer and reflection mirror) as the probe is introduced into the vessel of the patient's vascular system.

Miniaturization of ultrasonic imaging probes which are capable of providing real time images through 360° presents several technical obstacles. For example, due to the miniature size of the components, it has been found that rotation of the transducer and/or any reflective mirror must be effected with virtually no "play" being present—otherwise skewed and/or inconsistent alignment of the transmitted and returned ultrasonic energy may result. Such imprecise and/or inconsistent ultrasonic energy alignment may therefore deleteriously affect the signal-to-noise ratio of the electrical signals produced by the transducer which, in turn, could result in imprecise and/or unrecognizable images.

While it might be envisioned that mechanical bearings could be provided to ensure virtual absolute coaxial rotation of the transducer and/or mirror, in reality, such bearings are too large and cumbersome to be used in ultrasonic imaging probes of sufficiently miniaturized size for insertion into equally small sized blood vessels of a patient's cardiovascular system, for example. Hence, the use of such bearings as has been proposed in prior large scale ultrasonic imaging devices conventionally termed "endoscopes" (such as those disclosed in, for example, U.S. Pat. Nos. 4,572,201; 4,466,444; 4,442,842; and 4,391,282), is entirely inadequate for use in miniaturized intravascular ultrasonic imaging devices of the type contemplated by the present invention.

It is also necessary that the ultrasonic imaging probe does not pose an unreasonable risk to the patient during use. For this reason, any rotational components should be mechanically isolated from the tissue in the patient's intravascular system—e.g., so as to prevent inadvertent and/or undesired tissue abrasion which might otherwise occur during operation if the rotational components were "exposed" to the patient's tissue. However, mechanically isolating these components creates further technical hurdles since the ultrasonic waves must not be attenuated by the isolating structure to an extent which would disrupt the obtained image.

It is towards attaining solutions to the above-noted problems that the present invention is directed. Broadly, the present invention is directed to an ultrasonic imaging probe of sufficiently miniaturized dimensions which enable the probe to be used within vessels of a patient's cardiovascular system, and which is capable of providing an image of such vessels through 360° by rotation of a distally located transducer subassembly.

Important to the present invention, the transducer subassembly operates within a guide catheter previously positioned within the patient's intravascular system in a manner to be described in greater detail below. The guide catheter includes a distal section forming a "window" which minimally attenuates and/or reflects ultrasonic energy, and which mechanically isolates the rotational transducer subassembly from surrounding tissue. Perhaps equally significant, this distal region of the guide catheter serves the additional beneficial function of providing a distal bearing surface for the transducer subassembly and thereby ensures that virtual absolute coaxial rotation of the transducer subassembly relative to the guide catheter's axis will occur.

An essentially rigid tubular drive shaft is provided at the probe's proximal (and patient-external) end and is operatively connected to suitable motive means for imparting the desired rotation direction and velocity to the distally located transducer subassembly. In this regard, a torque cable interconnects the proximally located drive shaft and the distally located transducer subassembly so that the rotation direction and velocity of the former is transferred to the latter.

The torque cable employed in the probe of the present invention is formed of inner and outer subcables fabricated from wires which are helically wound in opposite directions relative to one another. Thus, the wires forming the inner and outer subcables are directionally wound such that their adjacent windings respectively tend to expand and contract radially when the subassembly is rotated in an intended rotational direction. This responsive expansion/contraction of the windings, in turn, effects an essentially rigid union between the inner and outer torque wires so that rotational movement provided by the motive means is reliably transferred to the transducer subassembly.

The preferred torque cable exhibits maximum strength under torsion, yet minimal strength under tension (i.e., exhibits minimal longitudinal stiffness). In order to increase the torque cable's longitudinal stiffness (i.e., increase its strength under tension), a suitable polymer material (e.g., low to medium density polyethylene) is impregnated into the interstices between the adjacent torque cable windings. Without such polymer impregnation, the torque cable may, during use, oscillate radially within the guide catheter and thereby cause the transducer subassembly to rotate at variable angular velocities. However, by increasing the longitudinal stiffness of the torque cable, essentially constant angular velocity may be transferred to the transducer subassembly since disturbing radial oscillations of the torque cable within the guide catheter will have been minimized (if not eliminated).

Additional longitudinal strengthening of the torque cable may be provided by means of at least one elongate strengthening element which is positioned within the torque cable, extends its entire longitudinal length, and is fixed to its proximal and distal ends. The strengthening element serves the beneficial function of longitudinally positionally fixing (tethering) the proximal and distal ends of the torque cable to thereby insure that it can easily be withdrawn from the patient without damage. And, in the unlikely event that the torque cable fails (e.g., severs) during use, the strengthening element will allow the entire torque cable to be withdrawn from the patient since it is connected to both the proximal and distal torque cable ends, thereby enhancing the safety of the probe assembly of this invention. Preferably, the strengthening element is in the form of at least one synthetic fiber monofilament.

In use, a conventional guide wire having a fluoroluminescent tip (e.g., formed of gold) will be inserted percutaneously into a desired vessel of a patient's vascular system, for example the patient's femoral artery, and is maneuvered so that its distal end is located in the particular vessel desired to be imaged. Progress of the guide wire can be visually followed by the attending physician using standard fluoroscopic techniques.

Next, the guide catheter is inserted telescopically over the now stationary guide wire. The guide catheter will preferably have a fluoroluminescent marking at its distal end so that the attending physician can similarly follow its progress over the guide wire using fluoroscopic imaging techniques. With the guide catheter properly positioned, the physician will then withdraw the guide wire so that the transducer subassembly can be inserted within the guide catheter's now vacant lumen.

It will be appreciated that the fluoroluminescent marking at the distal end of the guide catheter will provide a convenient stationary reference from which the physician can accurately position the transducer subassembly (which itself is entirely visible fluroroscopically). Thus, by operating the transducer subassembly, ultrasonic images corresponding to 360° "slices" of the vessel will be obtained. And, these images can be obtained along a longitudinal section of the vessel since the transducer is both rotationally and longitudinally moveable within the guide catheter.

Once ultrasonic imaging has been completed and the desired information obtained, the physician may withdraw the transducer subassembly from the guide catheter and leave the guide catheter in position. Thus, the guide catheter may be employed as a channel for the introduction of suitable therapeutic probes (e.g., low profile angioplasty devices) and/or the delivery of pharmaceuticals to treat the afflicted site in the patient's cardiovascular system. Thus, the guide catheter will provide a convenient common path for both diagnosis (via the transducer subassembly of this invention) and treatment (e.g., via use of a separate therapeutic device and/or pharmaceuticals) of afflicted sites in a patient's cardiovascular system.

The probe and the imaging technique briefly described above represent a significant departure from what is believed to be the current wisdom in this art. For example, as evidenced by Yock '931, the conventional wisdom in this art is to provide an "all-purpose" intravascular imaging probe—i.e., one that includes integral guide wire structures so that the entire probe can be inserted directly into the patient's vascular vessels. In direct contrast, the present invention relies on a conventional discrete guide wire which serves as a means to position a guide catheter, the latter defining an adequately sized lumen to later accept (i.e., when the guide wire is withdrawn leaving the guide catheter in place) the transducer subassembly. In this manner, the imaging probe of this invention is especially well suited for use in the tortuous paths of very small sized coronary arteries and solves many of the problems briefly discussed above which have plagued conventional probes used in intravascular ultrasonic imaging.

These advantages, and others, will become more clear after careful consideration is given to the following detailed description of the preferred exemplary embodiment.

BRIEF DESCRIPTION OF THE ACCOMPANYING DRAWINGS

Reference will hereinafter be made to the accompanying drawings wherein like reference numerals throughout the various FIGURES denote like structural elements, and wherein:

FIG. 2 is a longitudinal cross-sectional view showing the distal end of the probe of this invention, and more particularly, showing the transducer subassembly operatively associated within the guide catheter;

Figure 9:
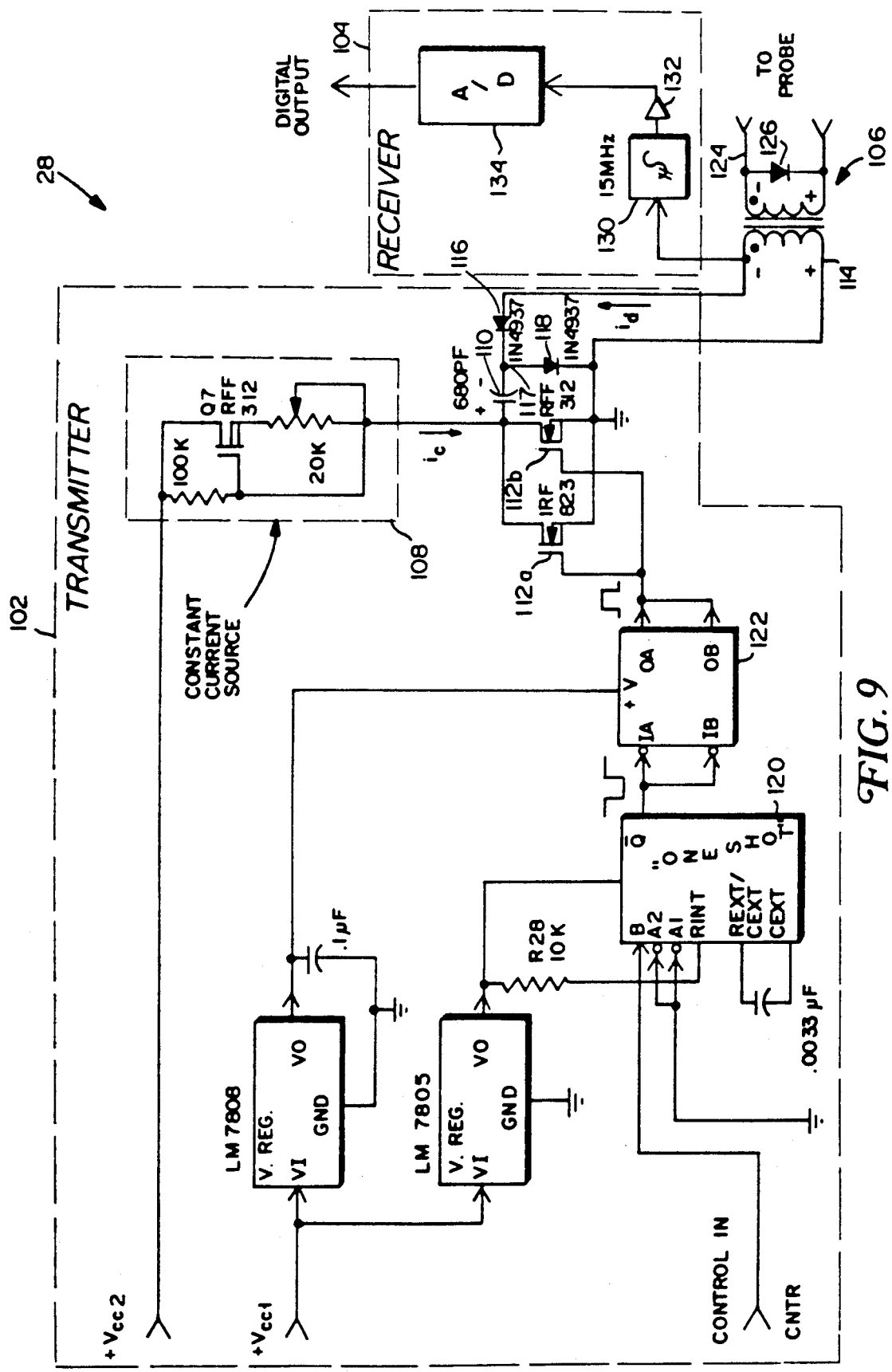

FIGS. 7a through 7d schematically depict the sequence of inserting the probe of this invention into a patient's vascular system;

FIG. 8 is a partial longitudinal cross-sectional elevational view particularly showing the guide catheter in place over the previously positioned guide wire (i.e., in a state shown in FIG. 7b); and FIG. 9 is a schematic diagram of the ultrasonic transceiver circuitry employed in the imaging system of the present invention;

FIGS. 10a and 10b are each representative photographs of video images of a pig femoral artery obtained using the ultrasonic imaging probes of this invention; and FIGS. 11a and 11b are each representative photographs of video images of a pig coronary artery using the ultrasonic imaging probes of this invention.

DETAILED DESCRIPTION OF THE PREFERRED EXEMPLARY EMBODIMENTS

Figure 1:
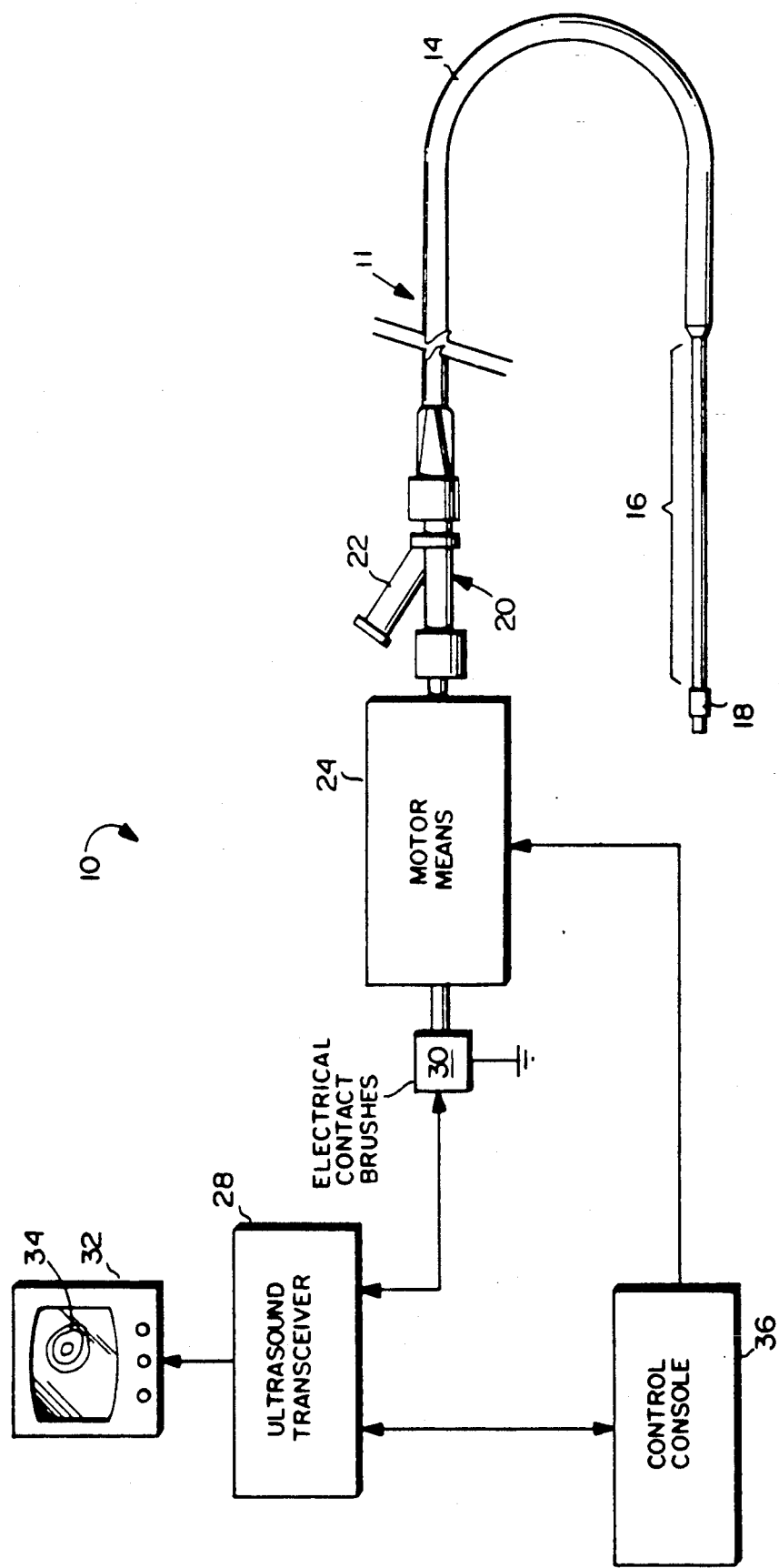
FIG. 1 is a schematic diagram of an exemplary ultrasound imaging system with which the ultrasound imaging probe of this invention is used.

A schematic diagram of an exemplary ultrasound imaging system 10 is shown in accompanying FIG. 1. System 10 generally includes an ultrasound imaging probe assembly 11 having a distal transducer subassembly 12 (not seen in FIG. 1, but see, for example, FIG. 2) inserted operatively within a guide catheter 14. The distal end of the guide catheter 14 includes a region 16 of reduced wall thickness (e.g., a wall thickness of about 0.005 inch (0.0127 cm) as compared to the wall thickness of catheter 14 of about 0.010 inch (0.0254 cm)) to provide a "window" that is relatively transparent to ultrasonic imaging waves (i.e., minimally attenuates and/or reflects ultrasonic energy). The longitudinal length of region 16 is advantageously about 2.0 inches (about 5.0 cm), with the overall length of catheter 14 (including the region 16) being about 11.8 inches (about 30 cm) for direct (e.g., arteriotomy) insertions, to about 59 inches (about 150 cm) for percutaneous distal insertions (e.g., via the femoral artery).

A fluoroluminescent band 18 (measuring about 0.020 inch (0.51 mm) in width and positioned about 0.040 inch (1.02 mm) from the terminal end of catheter 14) formed, for example, of gold or the like, is fixed (e.g., via crimping) onto the distal end of guide catheter 14 so that an attending physician, using conventional fluoroscopic techniques, can follow the progress of the catheter 14 during insertion into a patient's vascular system and/or to provide a reference for the ultrasonic imaging subassembly 12 once the guide catheter 14 has been properly positioned (as will be explained in greater detail below).

The proximal (and patient-external) end of the guide catheter 14 is coupled to a conventional Y-connector 20 having a port 22 through which saline solution may be introduced into the lumen 14a (see FIG. 2) of guide catheter 14. The ultrasonic imaging subassembly 12 is coupled to suitable motor means 24 via structures to be described in greater detail below. Suffice it to say here that the motor means 24 provides the drive for rotating the subassembly 12 and can be any suitable high speed precision motor. Preferably, the motor means is a variable precision motor capable of rotating the subassembly 12 between zero to about 1800 rpm.

Electrical communication with the imaging subassembly 12 is provided by a conventional two-lead microcoax cable 26 (see FIG. 2). During rotation, electrical communication is established between the ultrasonic imaging subassembly 12 (via the cable 26) and the ultrasound transceiver 28 (see FIG. 1) via suitable electrical contact brushes 30. The ultrasound transceiver 28 utilizes the circuitry to be discussed below with reference to FIG. 9, and produces a pulse signal (of desired magnitude and shape) which is applied via the cable 26 (through brushes 30) to excite an electroacoustic transducer 44 (see FIG. 2) housed within the imaging subassembly 12. The transceiver 28 also performs conventional signal processing operations (e.g., amplification, noise reduction and the like) on electrical signals generated by electro-mechanical excitation of the transducer 44 within the subassembly 12 (i.e., signals generated by the transducer in response to receiving echo waves).

These signals are further processed digitally via known display algorithms (e.g., conventional PPI (radar) algorithms) and are then supplied as an input to a CRT monitor 32 (or any other equivalent display device) so as to generate an ultrasound image 34 of desired format representative of the vascular structures reflecting ultrasonic energy toward the transducer within the subassembly 12. A control console 36 may be employed by the attending physician so as to select the desired operational parameters of the ultrasound transceiver 28 and/or the motor means 24.

Figure 3:
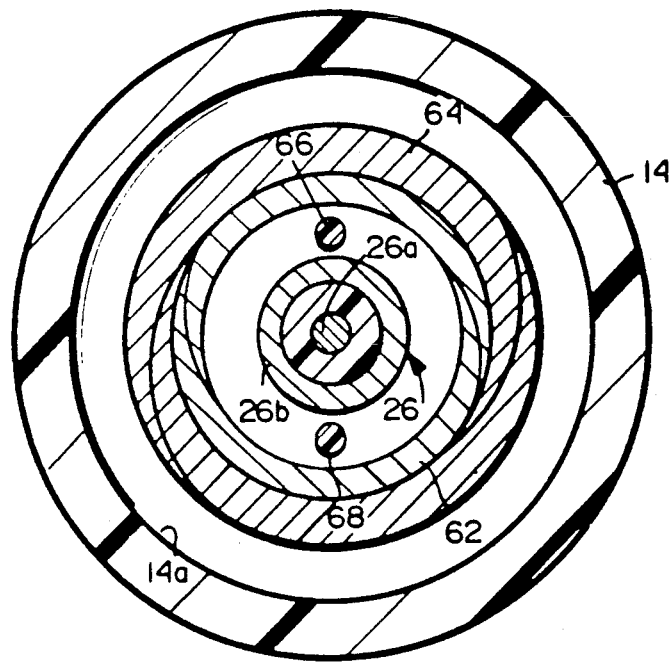
FIG. 3 is an enlarged latitudinal cross-sectional view of the probe of this invention as taken along line 3—3 in FIG. 2.
Figure 4:
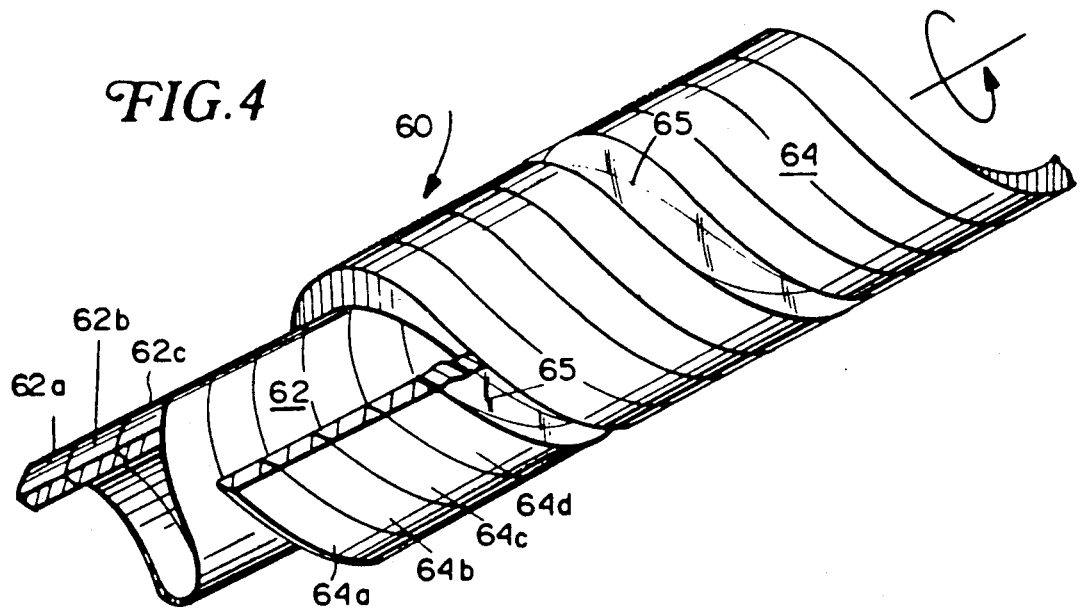
FIG. 4 is a detailed perspective view of a representative segment of the torque cable employed in the present invention.

The ultrasonic imaging subassembly 12 and the structures which serve to connect the same electrically and mechanically to the patient-external environment are shown in accompanying FIGS. 2–4. The distal end of the imaging probe of this invention is shown particularly in FIG. 2 as including the imaging subassembly 12 which is operatively received within the essentially cylindrical lumen 14a (having a preferred diameter of about 0.045 inch (1.17 mm)) of guide catheter 14. The subassembly 12 principally includes a rigid tubular housing 40 (having a preferred outside diameter of about 0.042 inch (1.07 mm)) which may be fabricated, for example, from conventional stainless steel hypodermic tubes.

An acoustic reflector 42 is rigidly coaxially positioned within the distal portion of housing 40, while an ultrasonic transducer 44 is rigidly and coaxially positioned within the proximal portion of housing 40 so as to be in facing relationship to the planar reflective surface 46 defined on the proximal end of the acoustic reflector 42. The distal end of the housing 40/acoustic reflector 42 is preferably formed into a smoothly convex tip 48 so as to assist in the guiding of the subassembly 12 through the lumen 14a of guide catheter 14.

The reflective surface 46 is preferably oriented at an angle (e.g., 45°) relative to the longitudinal axis of the tubular housing 40 so that ultrasonic waves emitted by the transducer 44 may be radially redirected towards the tissue to be imaged, while returning echo wave may be radially redirected along the longitudinal axis of the housing 40 towards the transducer 44. Although the surface 46 is preferably planar, it may be provided in other geometric forms, for example concave, particularly if convergent focussing of emitted/returned echo waves is desired. And, the angular orientation of surface 46 with respect to the longitudinal axis of housing 40 may be greater/lesser than 45° so as to project the reflected emitted acoustic waves in a proximal/distal direction relative to the subassembly, respectively, and/or to minimize orthogonal reflections of ultrasonic energy from the region 16 of the guide catheter 14. Preferably, the reflective surface 46 is formed of a highly polished stainless steel, but other suitable materials (e.g., quartz or sapphire) may be employed.

The transducer 44 is essentially similar to the transducers disclosed in the above-identified U.S. Pat. No. 4,841,977 in that it includes a generally cylindrical body 50 of a suitable piezoelectric material which is precision cut so as to resonate at a desired frequency (e.g., about 25 MHz). The piezoelectric body 50 should be made from a material with controlled porosity (i.e., minimal voids) so as to avoid short-circuit phenomena when the transducer is electrically contacted while ensuring mechanical integrity and meeting piezoelectric performance criteria (i.e., efficient conversion between electrical and mechanical energy). Preferably, the piezoelectric material forming the body 50 is selected from LZT-2, EBL-2 or PZT-5 ceramics, lead metaniobate, or magnesium niobate, with LZT-2 being particularly preferred due to the minimal presence of voids in such material. The axial and diameter dimensions of the transducer 44 are each preferably about 0.030 inch (0.762 mm).

A conductive metal faceplate 52 is deposited on the forward surface of the piezoelectric body 50 and extends proximally around an external circumferential portion of the latter. The faceplate 52 is preferably a multi-layer structure formed of an inner (i.e., adjacent the forward surface of the piezoelectric body 50) layer of copper, and intermediate layer of platinum, and an outer layer of gold. The platinum layer serves as a bonding layer for both the copper and the gold (since it exhibits adequate bonding properties for both such metals), while the gold layer serves to protect the underlying copper layer from oxidation. Conventional electrodeposition techniques are used to sequentially deposit these layers so that the total layer thickness of the faceplate 52 is approximately 1,000 to 10,000 Å (or more if required for good conductivity). The thickness of the faceplate 52 is, however, selected so that it is essentially one-fourth wavelength at the operating frequency o the piezoelectric body 50.

The transducer 44 is rigidly affixed within the proximal portion of housing 40 in any expedient fashion to ensure electrical contact between the housing 40 and the faceplate layer 52 (i.e., via that portion of faceplate layer 52 which extends proximally over a circumferential portion of the piezoelectric boy 50). In this regard, it is presently preferred to use an electrically conductive epoxy, for example, an epoxy which is loaded with an amount of conductive metal (e.g., silver) effective to obtain electrical conductivity. A number of suitable epoxy materials are commercially available, with the presently preferred epoxy being Insulcast 612A commercially available from Permagile Industries, Inc. of Plainview, N.Y.

The transducer 44 also includes a backing layer 54 approximately 0.030 inch (0.762 mm) thick formed of a material selected for its electrical conductivity and ultrasonic energy absorbing properties. Electrical conductivity is important for backing layer 54 so that the piezoelectric body 50 may be electromechanically vibrated in response to receiving stimulus from an electrical signal. The ultrasonic energy absorbing property of the backing layer 54 is important so that the transducer 44 is essentially unidirectional (i.e., the ultrasonic energy emitted by transducer 44 is maximized distally towards the acoustic reflector 42). Preferably a powdered dense electrically conductive material (e.g., tungsten powder) is incorporated into an epoxy in an effective amount to increase its acoustic impedance and to cause scattering of acoustic energy. The preferred epoxy materials for use as the backing material include those which cure at elevated temperatures.

The piezoelectric body 50 is electrically isolated from the housing 40 via an insulating sleeve 56 formed of any suitable electrically insulating epoxy material coated on its exterior circumferential surface. In this regard, it is preferred during fabrication to first coat the sleeve 56 onto the exterior circumferential surface of the body 50 prior to forming the faceplate and backing layers 52, 54, respectively. It will be observed in FIG. 2 that an annular region will be established between this insulating sleeve 56 and the interior of the housing 40, which space may be filled with a suitable electrically insulating epoxy to ensure adequate bonding between these structures and to enhance the mechanical integrity of the same.

Electrical communication with the transducer 44 and the ultrasonic controls located externally of the patient is accomplished by means of a microcoax (or other suitable two-lead) cable 26 located within the torque cable 60 (to be described below). Electrical contact and series connection with the transducer 44 is effected by soldering the inner lead 26a of cable 26 to the backing layer 54, and soldering a portion of the outer lead 26b to an interior region of the housing 40. Since the piezoelectric body 50 is electrically isolated from the housing (i.e., via insulating sleeve 56) and the faceplate is electrically connected to the housing (i.e., via an electrically conductive epoxy), merely soldering the outer conductor 26b to the housing 40 will place the transducer in series connection.

The preferred torque cable 60 will include inner and outer subcables 62, 64, respectively (see FIG. 4), formed of flat wires oppositely wound with respect to one another. The inner subcable 62 is preferably a trifilar—that is, formed of three flat metal wires 62a–62c preferably measuring in cross-section about 0.06 inch (1.5 mm) deep ×0.12 inch (3.0 mm) wide and tightly wound in a direction which tends to expand the windings radially when rotated in a counterclockwise direction (as viewed from the proximal end of the torque cable 60). The outer subcable 64, on the other hand, is preferably a quadfilar—that is, formed of four flat metal wires 64a-64d preferably measuring in cross-section about 0.08 inch (2.0 mm) deep × 0.12 inch (3.0 mm) wide and wound such that (i) a gap of approximately one wire width exists between adjacent windings, and (ii) the windings tend to contract radially when rotated in a counterclockwise direction.

The respective tendency of the inner and outer subcables 62 and 64 to expand and contract radially will therefore create, during rotation in a counterclockwise direction, a rigid union to be effected therebetween. Thus, the composite torque cable 60 effectively transfers rotational motion to the transducer subassembly 12. Of course rotation in the clockwise direction may also be provided, in which case the wires of the inner and outer subcables 62 and 64, respectively, are wound reverse to that shown in FIG. 4.

While the torque cable 60 is relatively strong under torsional forces, it is relatively weak longitudinally (e.g., under tension) and thus is extremely longitudinally flexible thereby allowing it to negotiate the tortuous paths of a patient's cardiovascular system. In order to increase the longitudinal strength (i.e., increase the longitudinal stiffness) of the torque cable, it is preferred that the interstices between adjacent windings of wires be impregnated with a thermoplastic polymer, such as low to medium density polyethylene. The impregnating polymer is represented by reference numeral 65 in FIG. 4, it being understood that the polymer 65 will also preferably be present in the small clearance interstices between the individual wire windings of subcables 62 and 64.

The polymer-impregnated windings of the torque cable will therefore be stiffer longitudinally as compared to the "bare" windings (i.e., windings of the torque cable which are not polymer-impregnated). As mentioned previously, the increased longitudinal stiffness of the torque cable helps to reduce radial oscillations of the torque cable within the catheter 14 during use (thereby ensuring that the transducer subassembly 12 is rotated at essentially constant angular velocity), in addition to allowing the torque cable (and hence the transducer subassembly) to be more easily longitudinally advanced within and/or withdrawn from the catheter 14.

Polymer-impregnation of the torque cable 60 may be accomplished in any convenient or expedient manner, for example, by spraying, dipping, padding and the like a molten polymer (i.e., at a temperature at or above its melting point) onto the torque cable 60 and then allowing the polymer to cool (which may be accomplished in air and/or via a water cooling bath) and solidify within the interstices of the torque cable windings. A presently preferred technique, however, is to telescopically position a small-diameter tube formed of the impregnating polymer over the torque cable 60, and then subject the polymer tube/torque cable 60 to elevated temperatures sufficient to melt the polymer tube and cause the molten polymer thereof to flow into the interstices between the windings of the torque cable 60.

Figure 5:
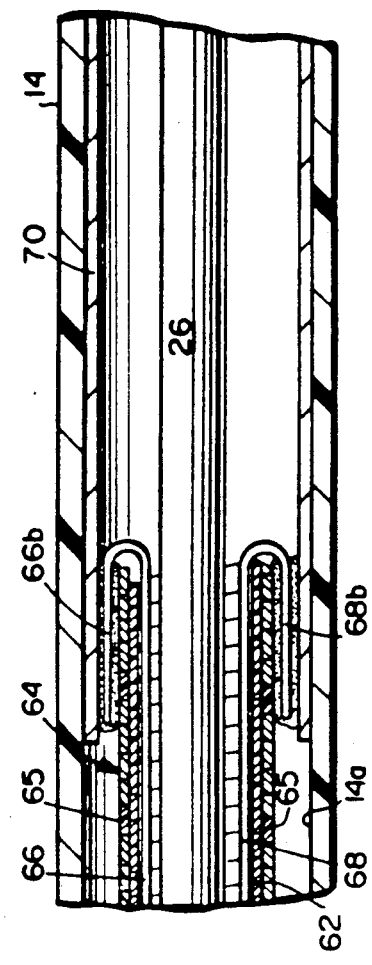
FIG. 5 is a longitudinal cross-sectional view showing the proximal end of the probe of this invention.

Additional longitudinal stiffness may be provided by means of one or more elongate fiber elements. Preferably, a pair of fibers 66, 68 are positioned in the annular space defined between the microcoax cable 26 and the inner subcable 62 of torque cable 60. The distal ends 66a, 68a of these fibers 66, 68 extend beyond the terminal end of the torque cable 60 and are disposed between the torque cable 60 and the interior of the housing 40, where they are embedded in an epoxy compound which also serves to rigidly affix the distal end of the torque cable 60 to housing 40. The proximal ends 66b, 68b of the wires 66, 68 and the proximal end of the torque cable 60 are similarly rigidly affixed to a tubular drive shaft 70 as shown in FIG. 5.

According to this invention, the preferred fibers are monofilaments formed of a synthetic resin, for example, an aromatic polyamide (e.g., Kevlar ® polyamide fiber commercially available from E.I. DuPont de Nemours & Co., Wilmington, Del.). Other suitable fibers may be employed, however. For example, the fibers 66, 68 may be multifilametary yarns and/or may be formed of a suitable metal.

As mentioned previously, the fibers 66, 68 serve to provide increased longitudinal strength for the torque cable 60 without adversely affecting its steerability within the guide catheter 14. In addition, however, the fibers 66, 68 function as a safety means to ensure that, in the event of a catastrophic failure of the torque cable 6 during use (e.g., severing), the transducer subassembly may nonetheless be withdrawn from the catheter 14. In this regard, it will be appreciated that, since the fibers 66, 68 are each fixed at their proximal and distal ends to the proximal and distal ends of the torque cable 60, the entire length of the torque cable will be tethered via the fibers 66, 68. Hence, the fibers 66, 68 provide a safety back-up in the event the breakage of the torque cable 60 due to the proximal and distal ends of the latter being tethered to one another via the former.

Figure 6:
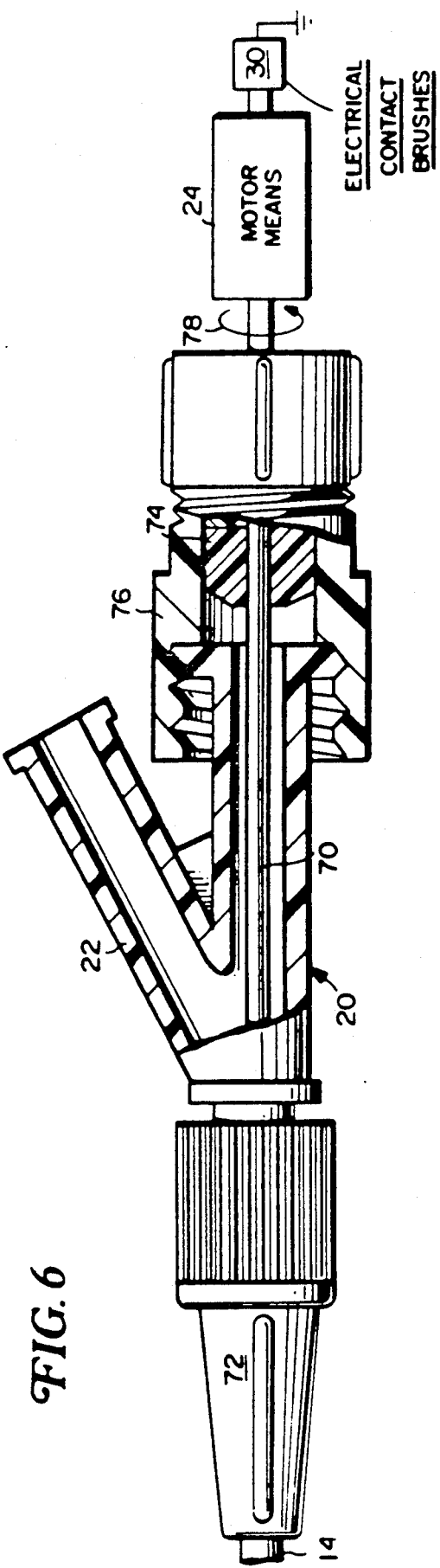
FIG. 6 is a longitudinal cross-sectional view in a scale smaller than that employed in FIG. 5 showing the proximal structures of the probe of this invention which are located externally of the patient during use.

The proximal end of the probe 11 according to this invention is shown more clearly in accompanying FIG. 6 as including a conventional Y-connector 20 having a port 22 through which a saline solution, for example, may be injected into the lumen of the guide catheter 14. The connector 20 and guide catheter 14 are coupled to one another via a conventional Leur lock 72. The drive shaft 70 is essentially rigid and is preferably fabricated from a conventional stainless steel hypodermic tube. The drive shaft 70 coaxially extends through the connector 20 and is operatively coupled to the motor means 24, with the microcoax cable 24 being operatively coupled to the electrical contact brushes 30. A length of the drive shaft 70 is supported and sealed via a synthetic resin bearing element 74 (housed within a proximal coupling 76) which serves as a proximal rotational bearing for the shaft 70 and also serves to seal the proximal end of connector 20 against saline fluid leakage. As briefly mentioned above, the motor means 24 will impart rotation to the drive shaft 70 (e.g., in a counterclockwise direction noted by the arrow 78 in FIG. 6), which in turn, is transferred to the subassembly 12 via the torque cable 60.

FIGS. 7a-7d schematically depict a preferred procedure for positioning the probe 11 of this invention within a vessel of a patient's vascular system (which is not shown for clarity of presentation). According to accepted medical procedures, the attending physician will first percutaneously insert a relatively large sized external guide tube (not shown) so as to assist in the later insertion of other catheters, guide wires, etcetera. For example, if a coronary artery is desired to be imaged, the physician will usually position the terminal end of the external guide tube adjacent the coronary ostium.

With the external guide tube in place (which will remain in place throughout the imaging procedure and any therapeutic procedure deemed necessary by the physician), a conventional tightly coiled guide wire 80 will be inserted within and through the external guide tube's lumen. The physician may monitor the progress of the guide wire 80 fluoroscopically due to the presence of a fluoroluminescent tip 82 at the guide wire's distal end. The guide wire 80 is maneuvered beyond the terminal end of the external guide tube until it is positioned at the desired location within the coronary artery to be investigated.

Figure 7A:
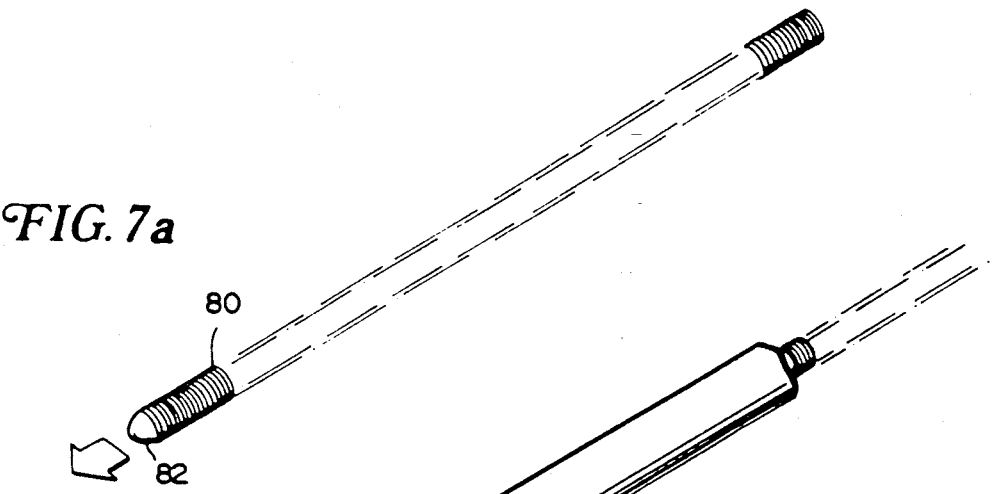
Figure 7B:
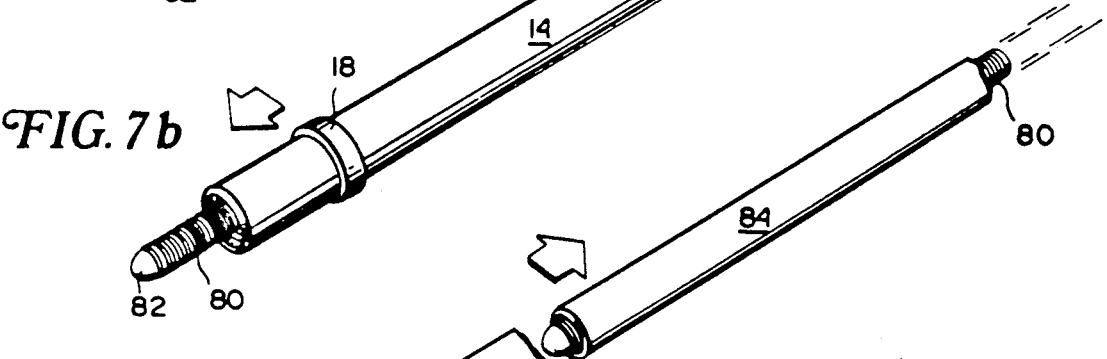
Figure 7C:
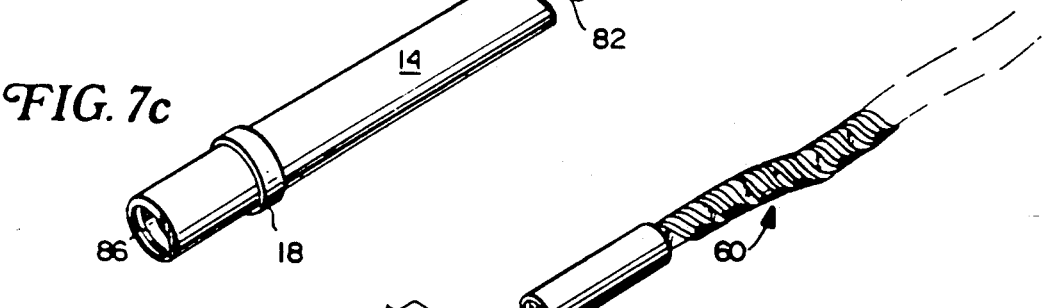
Figure 7D:
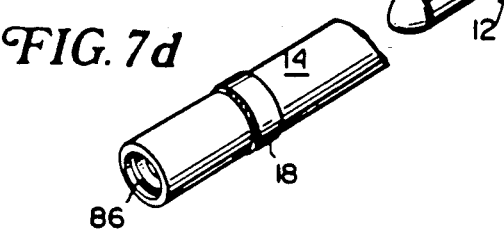

According to this invention, the guide catheter 14 having an inner removable tubular sleeve 84 (see FIGS. 7c and 8) is then telescopically inserted over the guide wire 80 as is shown schematically in FIG. 7b. The sleeve 84 is provided so that the effective internal diameter of the guide catheter 14 is reduced to accommodate the smaller diameter (i.e., as compared to the lumen 14a of guide catheter 14) guide wire 80 with slight clearance and thereby allow the composite catheter 14/sleeve 84 to be more easily telescopically inserted thereover. The sleeve 84 also serves the beneficial function of somewhat decreasing the inherent flexibility of the guide catheter 14. In this manner, the composite guide catheter 14/sleeve 84 will reliably slide over the external periphery of the guide wire 80 thereby minimizing potential "kinking" of the highly flexible guide catheter 14 which might otherwise occur if it alone was attempted to be inserted telescopically over the guide wire 80.

The progress of the guide catheter 14 may be monitored by the attending physician fluoroscopically due to the presence of the fluoroluminescent marking band 18 at the catheter's distal end. When the physician has determined that the guide catheter 14 has been properly positioned over the guide wire 80 (e.g., as is shown in FIG. 8), the guide wire 80 and the inner sleeve 84 are removed as a unit from the guide catheter 14 as shown schematically in FIG. 7c. As will be appreciated, the entire lumen 14a of the guide catheter 14 will then be exposed so that the physician can insert the transducer subassembly 12 thereinto. An annular interior stop 86 (see FIG. 2) of reduced diameter within the lumen 14a of catheter 14 prevents the transducer subassembly 12 from being advanced beyond the guide catheter's terminal end.

Using the marking band 18 as a reference, the physician will be able to predetermine the positioning of the subassembly 12 (and hence the positioning of the transducer 44/mirror surface 46) relative to the region of the vessel desired to be imaged and will be able to observe the movement and positioning of the transducer subassembly 12 since the subassembly 12 is itself visible via fluoroluminescent imaging. Once the subassembly is properly positioned, the motor means 24 is operatively coupled to the proximal end of drive shaft 70 and the imaging controls set so as to produce real or non-real time images (as may be desired by the attending physician) on a CRT screen, or other suitable monitoring devices.

Once an image of the afflicted region in the patient's coronary artery, for example, has been obtained, the attending physician may then desire to administer therapeutic treatment. In this regard, the guide catheter 14 of the present invention will provide a convenient channel for the physician to introduce (after the imaging subassembly 12 has been withdrawn form the catheter 14) a variety of suitable therapeutic devices and/or pharmaceuticals. For example, the physician may introduce a suitable low profile angioplasty device through the lumen 14a of catheter 14 and/or pharmaceuticals so as to treat the afflicted coronary artery. Thereafter, the physician may then reintroduce the subassembly 12 (after any therapeutic device has been withdrawn from the catheter 14) into the lumen 14a of catheter 14 and obtain ultrasonic images as discussed above, so as to determine the efficacy of the therapeutic treatment.

As briefly mentioned above, the distal section 16 establishes a region of catheter 14 which is relatively transparent (i.e., minimally attenuative and/or reflective) to ultrasonic energy. In this regard, the section 16 is of lesser cross-sectional outside diameter as compared to the remaining (proximal) section of catheter 14, while having essentially constant internal diameter throughout the length of catheter 14 and its distal section 16. This reduced wall thickness of section 16, collectively with the material from which is fabricated, contribute to providing a region of catheter 14 which minimally attenuates ultrasonic energy. It will also be observed that section 16 mechanically isolates the patient's surrounding tissue from the rotating transducer subassembly 12 thereby removing the possibility that the latter will abrade or injure such tissue.

The material from which the guide catheter 14 is made must therefore exhibit low ultrasonic energy reflectivity and attenuation, in addition to its being of sufficient flexibility to enable it to traverse the tortuous paths in a patient's cardiovascular system. Although a variety of candidate materials are available (e.g., low or medium density polyethylene, silicone, polyurethane, polyvinyl chloride, polytetrafluoroethylene and polyester), it is presently preferred to form the guide catheter 14 from low or medium density polyethylene (PE). Catheters formed of the preferred PE resin material are commercially available in a number of sizes, for example, from Putnam Plastics of Danielson, Conn.

The section 16 of the catheter 14 can be formed by locally heating (and thereby softening) the distal portion of catheter 14 and then drawing the softened distal catheter section 16 until the desired wall thickness is obtained. The preferred PE resin material forming the guide catheter 14 will also beneficially serve as a low friction bearing for rotation of the transducer subassembly 12.

As indicated previously, during use saline solution is capable of being injected into the lumen 14a of guide catheter 14 via the port 22 of Y-connector 20. The saline solution is preferably injected under positive pressure (relative to the vessel blood pressure in which the guide catheter 14 is located) so as to prevent blood from entering the guide catheter and thereby possibly clotting. In this regard, the saline solution will flow around the housing 40 between it and the interior surface of the guide catheter 14 so as to provide a lubricating medium for the housing 40 thereagainst during rotation of the subassembly 12. The saline solution will also fill the space between the faceplate 52 and the reflective surface 46 so as to provide a liquid acoustic coupling medium for the transducer subassembly 12.

FIG. 9 is a detailed schematic block diagram of an exemplary ultrasound transceiver circuit 28 for driving transducer 44 and for receiving signals from the transducer and converting them into digital signal form for real time imaging and/or other analysis.

Briefly, the preferred embodiment of system 10 excites transducer 24 so as to radiate relatively short duration acoustic bursts into the tissue surrounding probe assembly 11 while the transducer is rotating; receives the resulting ultrasonic "echo" signals reflected by the surrounding tissue (typically many such samples are received for each radiated pulse so as to obtain spatially-encoded image information for each excitation "radius"; and generates an image from the received echo signals. The preferred embodiment preferably generates images in real time using conventional image reconstruction/generation techniques (e.g., because of the advantages of presenting, to a physician, real time images of tissues encountered by the probe assembly 11 as the probe assembly traverses an artery or vessel and because no significant speed advantage is typically gained from merely collecting and storing data in real time for later image reconstruction/generation).

The resolution of the image provided by the preferred embodiment is dependent in large part upon the duration of the ultrasonic acoustic energy bursts emanated by transducer 44. It will be understood that the duration of a signal reflected by a particular structure of interest is determined by the duration of the envelope of an acoustic excitation burst striking that structure. Acoustic bursts having excessive durations (with respect to the dimensions of the smallest structure of interest) give rise to echo pulses having components attributable to reflection from tissue surrounding the structure as well as those attributable to the structure itself—preventing the image generation components from discriminating between the components and thus causing image blurring. Thus, it is desirable for the emanated acoustic energy bursts to have durations short enough such that each structure (or at least tissue interface) of interest reflects at least one pulse not substantially overlapped by pulses reflected by neighboring structures/interfaces.

In blood arteries, the smallest important structure of interest to a physician is typically the media, which has a width dimension of about 100 microns. To provide image resolution high enough to image this structure, the duration of transmitted acoustic pulse envelope can be no greater than about 125 ns. The envelope duration is determined by the characteristics of transducer 44 and by the duration of the electrical excitation pulse applied to the transducer. Preferably, transducer 44 is sufficiently damped to produce short duration pulses. In addition, the electrical excitation pulses applied to transducer 44 in the preferred embodiment are as short as possible (e.g., on the order of 20 ns) and while providing sufficient energy to maintain acceptable signal-to-noise ratio and sensitivity (since the signal-to-noise ratio and sensitivity of system 10 is degraded if acoustic pulses produced by transducer 44 have insufficient energy).

Transceiver circuit 100 in the preferred embodiment provides suitable short duration, high energy electrical excitation pulses to transducer 44, and efficiently and rapidly acquires multiple receive samples for each emanated acoustic pulse. Transceiver circuit 100 in the preferred embodiment includes a transmitter section 102, a receiver section 104, and a coupling transformer 106. Coupling transformer 106 couples signals from the transmitter section 102 to the transducer 44 (via the microcoax cable 26), and also couples signals from the transducer 44 to the receiver section 104. Transmitter section 102 generates very short duration excitation pulses to stimulate transducer 44 into emitting ultrasonic energy—and these pulses are coupled to the probe assembly 11 via the transformer 106.

The transducer 44 radiates the resulting ultrasonic energy into the surrounding tissue, and receives echoes from the tissue which it then converts into low-level electrical signals. These low-level electrical signals representing the received ultrasonic information are coupled to the receiver section 104 via transformer 106, are conditioned by receiver section 104 (e.g., to amplify and bandpass filter them), and are then converted into digital form (i.e., sampled at a rate of on the order of 200 times for each transmit pulse) for further processing using conventional image processing techniques.

The heart of exemplary transmit section 102 in the preferred embodiment of system 10 is a constant current source 108 charging a capacitor 110 which is then rapidly discharged (under control of transistors 112) through transformer 106 primary winding 114. Transistors 112 in the preferred embodiment are parallel connected FETs (e.g., type IRF823 and RRF312) which, when conducting, connect the "+"terminal of capacitor 110 to ground potential and which permit the "+"capacitor terminal to "float" when not conducting. The "−" terminal of capacitor 110 is connected at a "node" 117 to the cathode of a diode 116 and to the anode of another diode 118. The anode of diode 116 is connected to one side ("−") of the transformer primary winding 114, and the cathode of diode 118 is connected to ground potential. The "+" terminal of transformer primary winding 114 is connected to ground potential.

Constant current source 108 continually pumps a unidirectional current $i_c$ into the "+" terminal of capacitor 110, raising the potential existing at both the "+" and the "−" terminals of the capacitor above ground potential. This causes diode 116 to become reverse biased (to provide a very high degree of isolation between the transformer primary winding 114 "+" terminal and the transmitter section 102)—and also causes diode 118 to become forward biased (conducting). The conduction of diode 118 allows capacitor 110 to charge in response to the current produced by constant current source 108 and thus permits a difference in potential to develop across the plates of the capacitor. The supply voltage Vcc2 applied to constant current source 108 is selected so that a voltage potential of about 150 VDC builds up between the plates of capacitor 110.

A control (timing) signal CNTR applied to the input of a Schmitt triggered one-shot 120 (monostable multivibrator) causes a short duration pulse to be produced at the one-shot output (inverted Q). This control signal CNTR in the preferred embodiment comprises a transmit pulse generated in response to an angle sensor (not shown) coupled to torque cable 60 indicating the cable has rotated a certain incremental angle (e.g., 1/512 of a 360° rotation) since the last transmit pulse was generated.

In the preferred embodiment, this angle position sensor is part of motor means 24, and is used to indicate the angular position of transducer 44. It is thus important for torque cable 60 to rigidly transmit the torque produced by motor means 24 to the distal end of probe assembly 11—since otherwise the angle position sensor would not accurately indicate the position of transducer 44. To minimize changes in the relationship between the angular position of motor means 24 and the angular position of transducer 44, it is desirable that the angular velocity of the rotating cable be kept substantially constant. Of course, if the torque cable 60 does provide sufficient rigidity to transmit instantaneous changes in the motor means 24 angular velocity to the distal end of probe assembly 11, it may not be essential for angular velocity to be constant since the angular position sensor within motor means 24 would still accurately indicate the angular position of transducer 44.

There is, however, another reason for minimizing variations in the angular velocity of rotating torque cable 60. In the preferred embodiment (as mentioned above), transducer 44 is excited 512 times for each 360° rotation—and on the order of 200 samples are collected after each of the 512 excitations. The number of excitation/data collection cycles per rotation determines the circumferential resolution of the resulting image (i.e., the image resolution around the "circle" defining the image). While the number of excitations for each resolution should therefore be as high as practical, current technology (and in particular, commercial video RAM access speed) limits the rate at which data can be collected and processed using commonly available, relatively inexpensive components. The 512 excitations/revolution rate used in the preferred embodiment provides sufficient time between excitation pulses to permit a commercially available VRAM device to store on the order of 200 samples per excitation cycle. Loss of data would result if variations in the rotational velocity of torque cable 60 momentarily increased instantaneous velocity so that insufficient time was provided between adjacent angular increments for this data collection process to be performed. Of course, relaxation of the substantially constant angular velocity criterion is possible if loss of circumferential resolution can be tolerated.

In the preferred embodiment, the output pulse produced by one-shot 120 in response to the CNTR transmit pulse is further inverted and amplified by dual parallel-connected buffers 122 (e.g. type $SG_{3626}Y$) and is applied to the gates of transistors 112—thereby forcing the transistors to conduct. Conduction of transistors 112 effectively connects the "+" terminal of capacitor 110 to ground potential—forcing the potential at node 117 to become highly negative. Upon the potential at node 117 becoming negative, diode 118 becomes reverse biased (and thus ceases to conduct) and diode 116 becomes forward biased (and hence begins conducting). Thus, the result of turning transistors 112 ON is that charged capacitor 110 is connected directly across (and begins discharging through) the transformer primary winding 114.

In the preferred embodiment, only the impedance (resistance and reactance) seen at the transformer primary winding 114 limits the rate at which capacitor 110 discharges, and therefore a current $i_d$ of high magnitude almost immediately begins flowing through the primary winding upon turning transistors 112 ON. This causes a high-energy excitation signal with an extremely steep ("sharp") leading edge to be applied to transducer 44 by the transformer secondary winding 120 (a diode 126 connected across the secondary winding helps prevent the transducer from being exposed to excessive voltage levels).

In the preferred embodiment, one-shot 120 produces a pulse having a duration of about 25 microseconds (the duration of an single excitation/sampling cycle for a single transmit pulse). Due to the low impedance of primary transformer winding 114, the time required for the capacitor 110 to discharge virtually all of its stored charge into the transformer primary winding is only about 10-15 ns. The one-shot 120 continues to produce its output pulse long after the capacitor has discharged (i.e., during data collection) to short out high voltage noise through ON transistors 12 and to prevent feeding supply noise into the "front end" of receiver 104. Once the capacitor 110 has discharged to less than the voltage drop across the diode 116 PN junction, the diode once again becomes reverse biased (but may conduct certain noise pulses).

Transformer 106 in the preferred embodiment has a 1:1 turns ratio (primary to secondary) and includes a ferrite core with a permeability suitable to provide an excitation pulse trailing edge fall time duration of on the order of 8 nanoseconds (that is, it takes the excitation pulse applied to transducer 44 on the order of only 8 ns to fall to essentially zero amplitude). This fall time duration is selected to be as steep as possible in the preferred embodiment. The resulting excitation pulse applied to transducer 44 preferably has a duration of on the order of 20 ns or less (including rising and falling edges) and thus minimizes image "blurring" and increases image resolution by providing a short acoustic burst envelope duration (as described above).

While capacitor 110 is still shorted out, signals impressed upon the transformer secondary winding 124 due to ultrasonic "echo" signals received by the transducer 44 are passed through to the transformer primary winding 114 and on to the input of receiver section 104. Receiver section 104 preferably includes circuitry which isolates it from the high current pulses applied to the transformer primary winding 114 by discharge of capacitor 110. Receiver section 104 in the preferred embodiment further includes bandpass filter 130 comprising a 3-pole highpass filter 130 having 15 MHz corner frequency followed by a single-pole lowpass filter having a corner frequency of 30 MHz (thus providing a 15 MHz-30 MHz bandpass with roll-off of out-of-band signals below 15 MHz at 18 dB per octave and roll-off of signals above 30 MHz at 6 dB per octave). Bandpass filter 130 limits the signals used for imaging to a certain frequency band of interest (15-30 MHz in the preferred embodiment). These signals are amplified by a buffer amplifier 132 and converted into digital signals by an A/D converter 134 (preferably sampling at a rate of 30 to 100 MHz—well above the Nyquist rate of twice the excitation frequency of transducer 44). Images are produced from this resulting digital data in a conventional manner.

Photographs of ultrasonic video images of a pig's femoral and coronary arteries using the ultrasonic imaging system as above described are shown in FIGS. 10a-10b and 11a-11b, respectively. Each of the video images shown in FIGS. 10a-10b and 11a-11b were obtained at a data sampling rate of 38 MHz, with actual image size being about 8 mm. In each of these FIGURES, a dark circular region representing the diameter of subassembly 12 (where imaging is not possible) is visible, and is surrounded by an annular light region which is representative of the wall thickness of catheter region 16. The interior of the artery is then visible as a dark region outside of the initial light region with the artery wall visible as a larger diameter light region. In FIGS. 10a-10b, the arterial intima, media and adventitia tissue may be detected, with such tissue also being visible in certain radial sections of FIGS. 11a-11b.

As will be apparent, the present invention provides the means by which recognizable 360° ultrasonic intravascular images may be obtained. And, this imaging is accomplished using a procedure which ensures that the ultrasound transducer is properly positioned and operated without subjecting the patient to unreasonable risks associated with the imaging procedure. That is, tissue damage due to the rotating transducer subassembly is eliminated since the subassembly is mechanically isolated from the surrounding tissue via the guide catheter.

Thus, while the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. An ultrasonic imaging probe comprising:
   a guide catheter having an interior surface which defines a substantially cylindrical interior lumen;
   transducer means adapted to being positioned within said lumen of said guide catheter for producing acoustical signals in response to an electrical stimulus and for generating electrical signals in response to receiving echoes of said produced acoustical signals; and
   a flexible coiled torque cable means for rotating said transducer means coaxially relative to said guide catheter; wherein
   said guide catheter interior surface provides bearing means for establishing a bearing support for said transducer means during said rotation thereof; and wherein
   said flexible coiled torque cable includes at least one tether fiber having its proximal and distal ends respectively fixed to proximal and distal ends of said flexible coiled torque cable, whereby longitudinal stiffness of said torque cable is increased.

2. An ultrasonic imaging probe as in claim 1, wherein said means for rotating includes a helically wound wire torque cable means coupled to said transducer means.

3. An ultrasonic imaging probe as in claim 2, wherein said torque cable means includes polymer-impregnated inner and outer subcables formed of wires oppositely helically wound with respect to one another.

4. An ultrasonic imaging probe as in claim 3, wherein said oppositely helically wound wires of said inner and outer subcables provide means for radially expanding and contracting said inner and outer subcables in response to torsional force in a predetermined direction, whereby an essentially rigid union between said inner and outer subcables is effected due to said torsional force.

5. An ultrasonic imaging probe as in claim 2 or 3, wherein said at least one synthetic fiber comprises a pair of synthetic fibers each having proximal and distal ends fixed to respective proximal and distal ends of said torque cable means.

6. An ultrasonic imaging probe as in claim 5, wherein said synthetic fibers are each formed of an aromatic polyamide resin.

7. An ultrasonic imaging probe as in claim 1, wherein said transducer means includes:
   a housing,
   an acoustic transducer mounted in said housing, and
   acoustic reflector means mounted in said housing in coaxially opposing relationship to said transducer means for reflecting incident acoustic signals generated by said transducer between a first path which is essentially parallel to an axis of said housing, and a second path which is angularly oriented with respect to said first path, whereby
   acoustic signals produced by said transducer and propagating along said first path are redirected by said reflector means along said second path and toward an object to be imaged, and acoustic echo signals returning from said object to be imaged along said second path are redirected by said reflector means along said first path and toward said transducer.

8. An ultrasonic imaging probe as in claim 7, wherein said reflector means includes a planar surface oriented at an angle of substantially 45° relative to the axis of said housing axis.

9. An ultrasonic imaging probe as in claim 7, wherein said transducer is mounted proximally in said housing, and said acoustic reflector means is mounted distally in said housing.

10. An ultrasonic imaging probe comprising:
    housing means for holding an ultrasonic transducer; and
    torque cable means coupled to said housing means for transferring rotational motion in a predetermined rotation direction to said housing means;
    said torque cable means including an inner subcable and an outer subcable concentrically surrounding said inner subcable, said inner and outer subcables being formed of wires helically wound in opposite directions to provide means tending to radially expand and contract said inner and outer subcables, respectively, in response to rotation in said predetermined direction, whereby an essentially rigid union between said inner and outer subcables is effected to transfer torque to said housing means,
    said torque cable means also including means for increasing longitudinal stiffness of said torque cable means, wherein said means for increasing longitudinal stiffness of said torque cable means includes a polymer impregnated within interstices of adjacent windings of said helically wound inner and outer subcables.

11. An ultrasonic imaging probe comprising:
    housing means for holding an ultrasonic transducer; and
    torque cable means coupled to said housing means for transferring rotational motion in a predetermined rotation direction to said housing means;
    said torque cable means including an inner subcable and an outer subcable concentrically surrounding said inner subcable, said inner and outer subcables being formed of wires helically wound in opposite directions to provide means tending to radially expand and contract said inner and outer subcables, respectively, in response to rotation in said predetermined direction, whereby an essentially rigid union between said inner and outer subcables is effected to transfer torque to said housing means,
    said torque cable means also including means for increasing longitudinal stiffness of said torque cable means, wherein said means for increasing longitudinal stiffness of said torque cable means includes at least one synthetic fiber having proximal and distal ends fixed to respective proximal and distal ends of said torque cable means.

12. An ultrasonic imaging probe as in claim 11, wherein said at least one synthetic fiber comprises a pair of synthetic fibers each having proximal and distal ends fixed to respective proximal and distal ends of said torque cable means.

13. An ultrasonic imaging probe as in claim 12, wherein said synthetic fibers are each formed of an aromatic polyamide resin.

14. An ultrasonic imaging probe as in claim 10 or 11 wherein said housing means also holds an acoustic reflector in spaced, coaxially opposing relationship to said transducer.

15. An ultrasonic imaging probe as in claim 14, wherein said acoustic reflector and said transducer are rigidly affixed to said housing.

16. A medical probe comprising:
a distally located element;
a helically wound wire torque cable coupled to said distally located element and having relatively minimum strength longitudinally yet relatively maximum strength torsionally for transferring rotational motion to said element in a predetermined rotation direction; and
longitudinal strengthening means associated with said torque cable for increasing said relatively minimum longitudinal strength, wherein said longitudinal strengthening means includes at least one synthetic fiber fixedly attached at each of its ends to a respective end of said torque cable and extending within said torque cable between said fixedly attached ends thereof.

17. A probe as in claim 16, wherein said strengthening means includes a pair of synthetic fibers.

18. A probe as in claim 16, wherein said at least one said synthetic fiber is an aromatic polyamide fiber.

19. A probe as in claim 16, wherein further includes a polymer impregnated within interstices of said helically wound wire of said torque cable.

20. A probe as in claim 19, wherein said torque cable means includes inner and outer subcables formed of wires oppositely helically wound with respect to one another.

21. A probe as in claim 20, wherein said oppositely helically wound wires of said inner and outer subcables provide means for radially expanding and contracting said inner and outer subcables in response to torsional force in said predetermined rotation direction, whereby an essentially rigid union between said inner and outer subcables is effected due to said torsional force.

22. A probe as in claim 16, wherein said element includes a transducer subassembly which holds an ultrasonic transducer.

23. A probe as in claim 22, wherein said torque cable means includes:
an inner torque cable formed of wire helically wound in a first direction;
an outer torque cable formed of wire helically wound in a second direction opposite to said first direction; and
said first and second helical winding directions providing means for radially expanding and contracting said inner and outer torque subcables, respectively, in response to rotation in said predetermined rotation direction, and wherein
said strengthening means includes a polymer impregnated within said first and second helical windings.

24. A probe as in claim 23, wherein said transducer subassembly includes an acoustic reflector coaxially positioned in spaced relationship to said transducer.

25. A probe as in claim 24, wherein said transducer is rigidly affixed at a proximal location in said subassembly, and said acoustic reflector is rigidly affixed at a distal location in said subassembly.

26. An ultrasonic imaging system for obtaining real time images of a vessel in a patient's vascular system comprising:
a guide catheter defining a catheter lumen and adapted to being inserted into a vessel of a patient's vascular system;
ultrasonic imaging probe means adapted to being inserted within said catheter lumen for producing acoustical signals in response to an electrical stimulus and for generating electrical signals in response to receiving echoes of said produced acoustical signals returning from the vessel;
motive means for providing rotational drive to said imaging probe means to rotate the same in a predetermined rotation directing;
an ultrasonic transceiver coupled to said probe means including (i) transmitter means for generating said electrical stimulus and (ii) receiver means for receiving and interpreting said electrical signals produced by said probe means at a rate that is asynchronous relative to said generated electrical stimulus; and
electrical cabling which establishes electrical communication between said ultrasonic transceiver and said probe means for supplying said electrical stimulus to said probe means and for transmitting said electrical signals to said ultrasonic transceiver.

27. A system as in claim 26, wherein a distal region of said catheter lumen provides a bearing surface for said imaging probe means during rotation thereof.

28. A system as in claim 26, wherein said ultrasonic transceiver includes:
a transformer having a secondary winding electrically coupled to said probe means and having a primary winding;
capacitor means for storing an electrical charge; and
switching means operatively coupled to said capacitor means and to said transformer primary winding for permitting said capacitor means to intermittently discharge through said transformer primary winding.

29. A system as in claim 26, wherein said ultrasonic transceiver includes:
transformer means for coupling electrical signals to and from said probe means, said transformer means having at least one winding;
capacitor means for storing an electrical charge; and
switching means operatively coupled to said capacitor means and to said transformer means winding for selectively coupling said capacitor means across said transformer winding.

30. A system as in claim 26, wherein said ultrasonic transceiver includes high energy pulse generating means for periodically applying high energy, short duration electrical pulses to said probe means.

31. A system as in claim 30, wherein said pulses have a duration on the order of 20 ns or less.

32. A system as in claim 30, wherein said ultrasonic transceiver means further includes ferrite core means for limiting the fall time of each said pulses.

33. A system as in claim 26, wherein said ultrasonic transceiver includes:
transformer means for coupling electrical signals to and from said probe means; and
capacitive discharge means for coupling high amplitude electrical current to said transformer means in response to receipt of a timing control signal.

34. A method for ultrasonically imaging a portion of a vessel in a patient's vascular system comprising the sequential steps of:

percutaneously inserting a guide wire within the vessel to be imaged;

telescopically advancing a guide catheter having (i) a guide sheath with a distally located region which minimally attenuates and/or reflects ultrasonic energy, and (ii) a removable inner sleeve member such that said region is adjacent to the vessel portion to be imaged;

withdrawing said guide wire and said inner sleeve member from said guide sheath;

inserting an ultrasonic imaging probe within said guide sheath so that an ultrasonic transducer means associated with said probe is aligned with said distally located region which minimally attenuates and/or reflects ultrasonic energy; and then operating said transducer means to obtain ultrasonic images of said vessel portion.

35. A method as in claim 34, wherein said step of operating said transducer means includes rotating said transducer means within said guide catheter in a predetermined rotation direction.

36. A method as in claim 34, wherein said step of withdrawing said guide wire and sleeve member includes withdrawing said guide wire and said sleeve member as a unit.

37. A method as in claim 34, which further comprises removing said ultrasonic imaging probe from said guide catheter, and then administering a therapeutic procedure for said imaged vessel portion through said guide catheter.

38. A method for ultrasonically imaging a portion of a vessel in a patient's vascular system comprising the sequential steps of:

percutaneously inserting and positioning a flexible guide wire within a preselected vessel of a patient's vascular system to be imaged;

telescopically advancing a guide catheter over said guide wire and positioning a distal region of the same adjacent a portion of said preselected vessel to be imaged;

withdrawing said guide wire from said guide catheter; and then inserting an ultrasonic imaging probe into said guide catheter and operating said probe to obtain an ultrasonic image of said preselected vessel portion; wherein said step of advancing a guide catheter includes using a guide catheter having a removable inner tubular sleeve member sized so as to be capable of being telescopically advanced over said positioned guide wire; and wherein said step of withdrawing said guide wire includes withdrawing said inner tubular sleeve member.

39. A method as in claim 38, wherein said guide wire and said sleeve member are withdrawn as a unit.

40. A method as in claim 38, wherein said step of operating said probe includes rotating said probe within said guide catheter.

41. An ultrasonic imaging probe comprising:

a flexible wound wire torque cable defining an interior space between its proximal and distal ends;

an ultrasonic transducer carried at said distal end said torque cable;

electrical cabling disposed within said defined interior space of said torque cable and operatively connected to said ultrasonic transducer at said distal end thereof; and at least one fiber having a length substantially coextensive with said torque cable, said fiber being disposed within said defined interior space and having each of its ends fixed to a respective proximal and distal ends of said torque cable.

42. An ultrasonic imaging probe as in claim 41, wherein said at least one fiber includes a pair of synthetic fibers are provided within said defined interior space each with its ends respectively fixed to said proximal and distal ends of said torque cable.

43. An ultrasonic imagining probe as in claim 41 or 42, wherein said fiber is a monofilament synthetic fiber.

44. An ultrasonic imagining probe as in claim 41 or 42 wherein said fiber is a multifilamentary synthetic yarn.

45. An ultrasonic imagining probe as in claim 41 or 42, wherein said fiber is a metal fiber.

46. An ultrasonic imaging system for obtaining real time images of a vessel in a patient's vascular system comprising:

an ultrasonic imaging probe having an ultrasonic transducer at a distal end thereof which produces acoustical signals in response to an electrical stimulus and generates electrical signals in response to receiving echoes of said produced acoustical signals returning from the vessel;

a rotational drive element coupled to the ultrasonic imaging probe to rotate the same in a predetermined rotation direction;

an ultrasonic transceiver coupled operatively to said ultrasonic transducer and including (i) a transmitter which generates said electrical stimulus, and (ii) a receiver which receives said electrical signals produced by said ultrasonic transducer and interprets said received electrical signals at a rate which is asynchronous relative to said generated electrical stimulus; and electrical cabling which establishes electrical communication between said ultrasonic transceiver and said ultrasonic transducer for supplying said electrical stimulus to said ultrasonic transducer and for transmitting said electrical signals to said ultrasonic transceiver.

47. A system as in claim 46, wherein said ultrasonic transceiver includes:

a transformer having a secondary winding electrically coupled to said probe and having a primary winding;

a capacitor for storing an electrical charge; and a switch operatively coupled to said capacitor and to said transformer primary winding to permit said capacitor to intermittently discharge through said transformer primary winding.

48. A system as in claim 46, wherein said ultrasonic transceiver includes:

a transformer which couples electrical signals to and from said probe, said transformer having at least one winding;

a capacitor which stores an electrical charge; and a switch which is coupled operatively to said capacitor and to said at least one winding of said transformer to selectively couple said capacitor across said transformer.

49. A system as in claim 46, wherein said ultrasonic transceiver includes a high energy pulse generator which periodically applies high energy, short duration electrical pulses to said probe.

50. A system as in claim 49, wherein said pulses have a duration on the order of 20 ns or less.

51. A system as in claim 49, wherein said ultrasonic transceiver further includes a ferrite core for limiting the fall time of each said pulse.

52. A system as in claim 46, wherein said ultrasonic transceiver includes:

a transformer which couples electrical signals to and from said probe; and a capacitive discharge element which couples high amplitude electrical current to said transformer in response to receipt of a timing control signal.

* * * * *